United States Patent
Ichimura

(10) Patent No.: US 11,963,665 B2
(45) Date of Patent: Apr. 23, 2024

(54) ENDOSCOPE AND ENDOSCOPE SYSTEM

(71) Applicant: OLYMPUS MEDICAL SYSTEMS CORP., Tokyo (JP)

(72) Inventor: Hironobu Ichimura, Koganei (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 172 days.

(21) Appl. No.: 17/512,209

(22) Filed: Oct. 27, 2021

(65) Prior Publication Data
US 2023/0127909 A1    Apr. 27, 2023

(51) Int. Cl.
*A61B 1/015*    (2006.01)
*A61B 1/00*    (2006.01)
*A61B 90/00*    (2016.01)

(52) U.S. Cl.
CPC .......... *A61B 1/015* (2013.01); *A61B 1/00018* (2013.01); *A61B 1/00045* (2013.01); *A61B 1/00057* (2013.01); *A61B 2090/064* (2016.02)

(58) Field of Classification Search
CPC ............ A61B 1/00066; A61B 1/00108; A61B 1/00119; A61B 1/00135; A61B 1/012; A61B 1/015; A61B 1/018; A61B 1/05; A61B 1/051; A61B 1/053; A61B 1/126; A61B 2090/064; A61B 2562/0247; A61B 2562/0261; A61M 25/003; A61M 2025/0004; A61M 2025/0039; A61M 2025/0175
See application file for complete search history.

(56) References Cited

U.S. PATENT DOCUMENTS

| | | | |
|---|---|---|---|
| 2003/0176761 A1* | 9/2003 | Brady | A61B 5/4255 600/29 |
| 2005/0085695 A1* | 4/2005 | Shener | A61B 1/00071 600/156 |
| 2008/0294008 A1* | 11/2008 | Toyama | A61B 1/015 600/156 |
| 2009/0107503 A1* | 4/2009 | Baran | A61M 16/042 128/207.14 |
| 2012/0253124 A1* | 10/2012 | Torisawa | A61B 1/126 600/118 |

(Continued)

FOREIGN PATENT DOCUMENTS

| | | |
|---|---|---|
| JP | 2007-508871 A | 4/2007 |
| JP | 2021-058422 A | 4/2021 |
| WO | 2020/131461 A1 | 6/2020 |

OTHER PUBLICATIONS

English abstract only of WO 2005/037088 A2.

*Primary Examiner* — Aaron B Fairchild
*Assistant Examiner* — Stephen Floyd London
(74) *Attorney, Agent, or Firm* — Scully, Scott, Murphy & Presser, P.C.

(57) ABSTRACT

An endoscope includes an insertion portion including a distal end portion in which an image pickup unit is disposed, the insertion portion being configured to be inserted into an organ of a subject, an operation portion disposed at a proximal end of the insertion portion, and a sensor disposed in the operation portion, the sensor being configured to detect a pressure of a fluid in a flow passage passing through from the operation portion to a first opening of the distal end portion, the flow passage being configured to allow the fluid flowed into the operation portion to be flowed out from the first opening.

20 Claims, 5 Drawing Sheets

(56) References Cited

U.S. PATENT DOCUMENTS

| | | | |
|---|---|---|---|
| 2013/0303852 A1* | 11/2013 | Hiraga | A61B 1/00094 |
| | | | 600/118 |
| 2015/0133800 A1* | 5/2015 | McCaffrey | A61M 25/00 |
| | | | 600/486 |
| 2015/0314111 A1* | 11/2015 | Solar | A61M 25/1011 |
| | | | 604/509 |
| 2016/0317000 A1* | 11/2016 | Hassidov | A61B 1/126 |
| 2020/0069152 A1* | 3/2020 | Kasumi | A61B 1/0684 |
| 2020/0187768 A1* | 6/2020 | Shelton | A61B 17/32002 |
| 2020/0196839 A1 | 6/2020 | Pereira et al. | |
| 2021/0244267 A1* | 8/2021 | Shtul | A61B 1/126 |
| 2022/0168512 A1* | 6/2022 | Teh | A61M 39/10 |

* cited by examiner

ENDOSCOPE AND ENDOSCOPE SYSTEM

BACKGROUND OF THE INVENTION

1. Field of the Invention

The present invention relates to an endoscope that estimates pressure in an organ and an endoscope system that estimates pressure in an organ.

2. Description of the Related Art

Endoscopes are widely used in the medical field and the industrial field. In an endoscope used in the medical field, an insertion portion is inserted into a body of a subject to observe an inside of an organ and treat the organ using a treatment instrument inserted into a forceps channel and projecting from a distal end portion of the insertion portion.

For example, in treatment of renal calculus, an insertion portion of a ureteropelvic endoscope (a ureteropelvic videoscope) is inserted into a renal pelvis through a ureter. Thereafter, a laser probe, which is a treatment instrument, is passed through a forceps channel passing through the insertion portion. A calculus is broken by irradiation of laser light.

Visibility of the endoscope is sometimes deteriorated by a calculus fragment, bleeding, and the like. Accordingly, perfusate is injected into the renal pelvis through the forceps channel. The perfusate injected into the renal pelvis flows out to an outside of a body through an access sheath through which the insertion portion is passed.

Japanese Patent Application Laid-Open Publication No. 2021-58422 discloses a system that manages a balance between a supply amount and an outflow amount of perfusate in order to appropriately maintain a renal pelvis internal pressure.

U.S. Patent Application Publication No. 2020/0196839 discloses an endoscope in which a pressure sensor is disposed at a distal end portion of an insertion portion to detect an internal pressure of an organ.

SUMMARY OF THE INVENTION

An endoscope in an embodiment includes: an insertion portion including a distal end portion in which an image pickup unit is disposed, the insertion portion being configured to be inserted into an organ of a subject; an operation portion disposed at a proximal end of the insertion portion; and a sensor disposed in the operation portion, the sensor being configured to detect a pressure of a fluid in a flow passage passing through from the operation portion to a first opening of the distal end portion, the flow passage being configured to allow the fluid flowed into the operation portion to be flowed out from the first opening.

An endoscope system in an embodiment includes: an endoscope including an insertion portion including a distal end portion in which an image pickup unit is disposed, the insertion portion being configured to be inserted into an organ of a subject, an operation portion disposed at a proximal end of the insertion portion, a sensor disposed in the operation portion, the sensor being configured to detect a pressure of a gas in a flow passage passing through from the operation portion to a first opening of the distal end portion, the flow passage being configured to allow the gas flowed into the operation portion to be flowed out from the first opening into the organ, and a forceps channel disposed in the flow passage; a gas supply unit configured to supply the gas to the flow passage; a liquid supply unit configured to supply perfusate to the forceps channel; and an access sheath through which the insertion portion is passed, the perfusate injected into the organ from the first opening being flowed out to an outside of a body through a gap between the access sheath and the insertion portion.

DETAILED DESCRIPTION OF THE PREFERRED EMBODIMENTS

Figure 1:
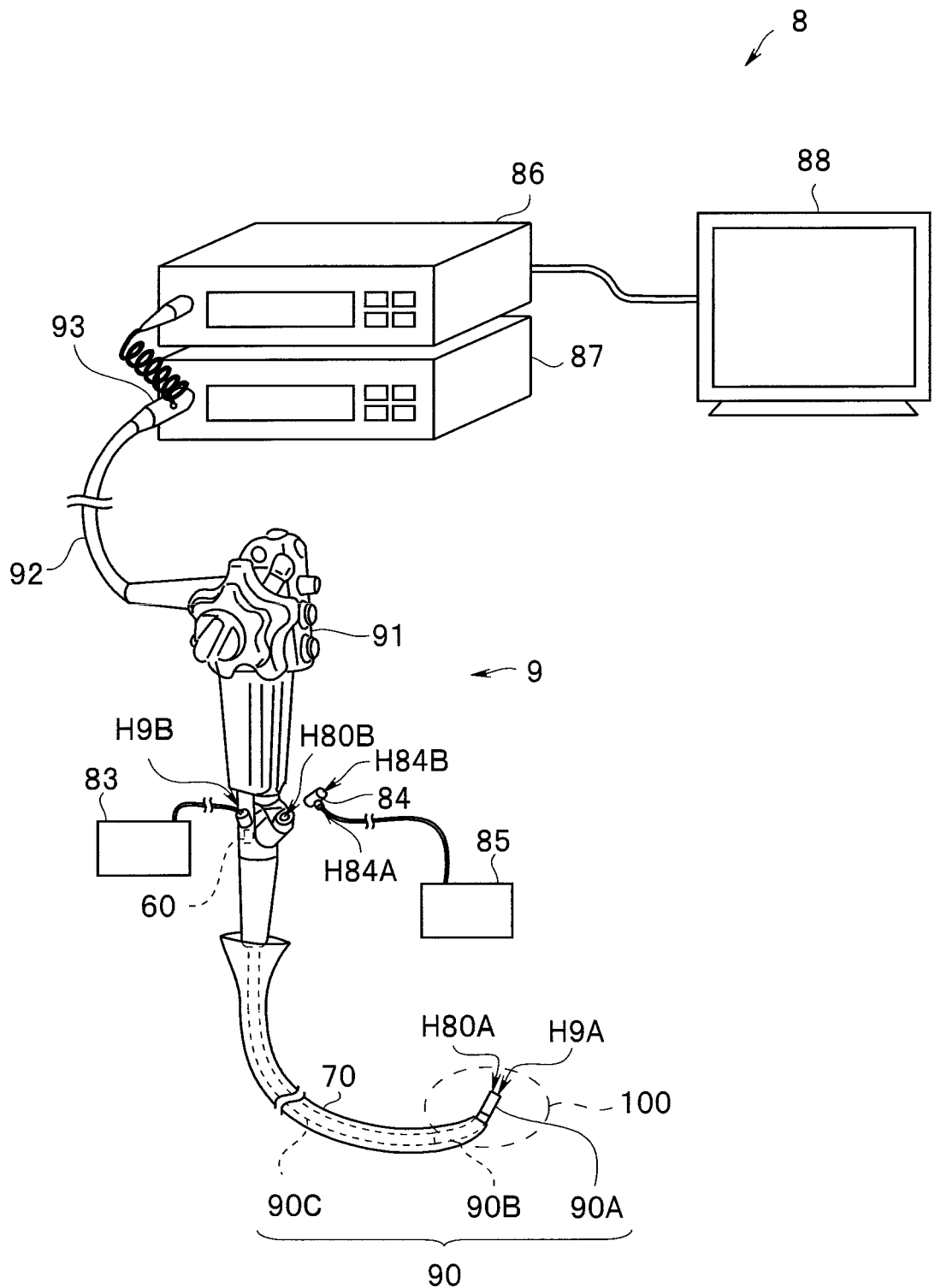
FIG. 1 is a perspective view of an endoscope system including an endoscope in a first embodiment.

Embodiments of the present invention are explained with reference to the drawings. The drawings based on the embodiments are schematic diagrams. In the drawings, relations between thicknesses and widths of respective portions, ratios of the thicknesses and relative angles of the respective portions, and the like are different from real ones. Portions, relations and ratios of dimensions of which are different, are included among the drawings. Illustration of and imparting of signs to some components are omitted.

First Embodiment

Figure 2:
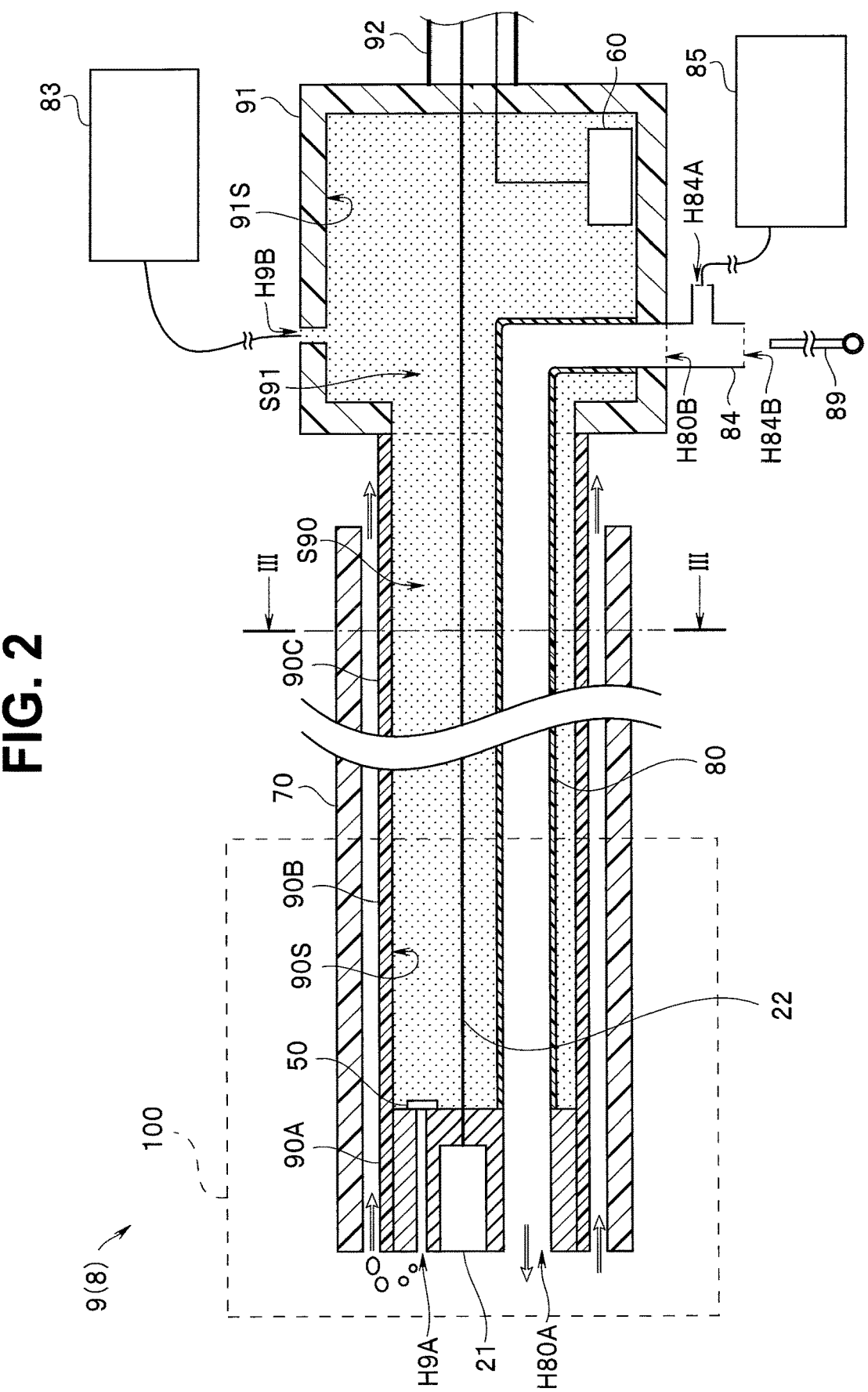
FIG. 2 is a sectional view of a main part of the endoscope system including the endoscope in the first embodiment.

As shown in FIG. 1 and FIG. 2, an endoscope 9 in the embodiment configures an endoscope system 8 in conjunction with an access sheath 70, a processor 86, a light source apparatus 87, a monitor 88, a gas supply unit 83, and a liquid supply unit 85. The endoscope 9 is a ureteropelvic videoscope.

The endoscope 9 includes an insertion portion 90, an operation portion 91, a universal cord 92, and a connector 93. When the insertion portion 90 of the endoscope 9 is inserted into a renal pelvis 100 through a ureter together with the access sheath 70, the endoscope 9 photographs an image of an inside of the renal pelvis and outputs an image signal.

The insertion portion 90 includes a distal end portion 90A, a bending section 90B disposed at a proximal end of the distal end portion 90A, and a flexible tube 90C disposed at a proximal end of the bending section 90B. An image pickup unit 21 including an image pickup optical system and a CCD image sensor, the image pickup unit 21 photographing an image, is disposed at the distal end portion 90A. The distal end portion 90A includes a distal end opening H80A of a forceps channel 80 passing through the insertion portion 90. The bending section 90B is bent by operation of the operation portion 91.

In the operation portion 91, various buttons for operating the endoscope 9 are provided. The operation portion 91 includes an insertion port H80B, which is an opening of the forceps channel 80. A T-shaped tube 84 is disposed in the insertion port H80B.

As explained below, the operation portion 91 includes an internal space S91 (FIG. 2) in which a sensor 60 for estimating a renal pelvis internal pressure, which is an organ internal pressure, is disposed. The sensor 60 is, for example, a pressure sensor in which a piezoelectric element is disposed in a membrane film that closes an opening of a sealed space. Electric resistance of the piezoelectric element changes because of deformation of the membrane film. The sensor 60 detects, from the electric resistance change of the piezoelectric element, pressure applied to an outer surface of the membrane film.

The access sheath 70 is a flexible tube having an inner diameter larger than an outer diameter of the insertion portion 90. The insertion portion 90 is passed through an inside of the access sheath 70. A proximal end of the access sheath 70 is disposed on an outside of a body.

The light source apparatus 87 has, for example, a white LED. Illumination light emitted by the light source apparatus 87 passes through a light guide 31 (see FIG. 3) passing through the universal cord 92 and the insertion portion 90 to thereby be guided to the distal end portion 90A and illuminates a subject. The light guide 31 includes a plurality of optical fibers.

The endoscope 9 transmits an image pickup signal outputted by the image pickup unit 21 disposed at the distal end portion 90A of the insertion portion 90 to the processor 86 through a signal cable 22. The processor 86 processes the image signal and outputs an endoscopic image to the monitor 88. The processor 86 performs control of the entire endoscope system 8 as well.

The liquid supply unit 85 supplies perfusate, which is liquid such as physiological saline. The perfusate is fed into the forceps channel 80 from an opening H84A of the T-shaped tube 84 disposed in the insertion port H80B of the operation portion 91 and is injected into the renal pelvis 100 from the distal end opening H80A of the distal end portion 90A. The renal pelvis 100 is filled with the perfusate. The perfusate injected into the renal pelvis 100 flows out to the outside of the body through a gap between the access sheath 70 and the insertion portion 90.

When an injection amount of the perfusate is larger than an outflow amount of the perfusate, the renal pelvis internal pressure rises. Accordingly, it is necessary to appropriately manage the injection amount of the perfusate based on the renal pelvis internal pressure.

Figure 3:
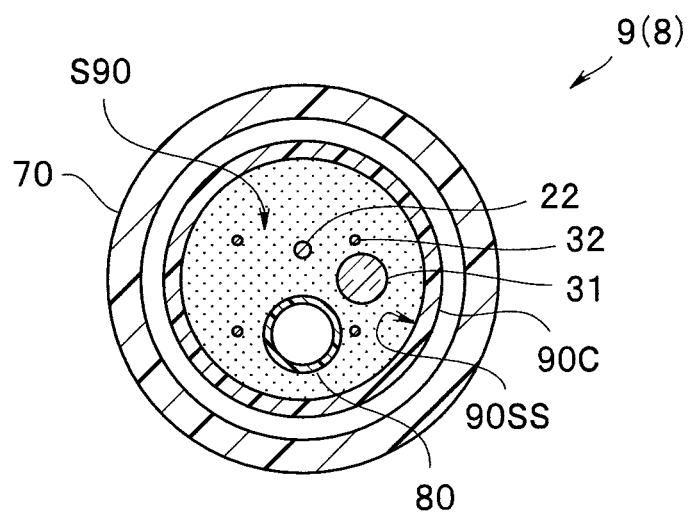
FIG. 3 is a sectional view taken along a line of FIG. 2.

As shown in FIG. 3, in an internal space S90 of the insertion portion 90, the signal cable 22, the forceps channel 80, operation wires 32 for bending the bending section 90B, the light guide 31, and the like are disposed. The endoscope 9 includes four operation wires 32 for the endoscope 9 to bend in four directions. An endoscope configured to bend in two directions includes two operation wires 32. The signal cable 22, the operation wires 32, and the like may be disposed in respective tubes or may be disposed in a multi-lumen tube.

For example, the internal space S91 of a housing of the operation portion 91 made of hard resin or the like communicates with the internal space S90 of the tubular insertion portion 90 made of soft resin, mesh-like metal, and the like.

The gas supply unit 83 supplies gas, for example, air for estimating an internal pressure of the renal pelvis 100. Although not shown, the liquid supply unit 85 and the gas supply unit 83 are connected to the processor 86 and controlled by the processor 86.

The endoscope 9 includes, at the distal end portion 90A, a first opening H9A communicating with the sealed internal space S90 of the insertion portion 90. The operation portion 91 includes a second opening H9B communicating with the sealed internal space S91. The internal space S90 of the insertion portion 90 and the internal space S91 of the operation portion 91 communicate with each other.

A gas feeding tube of the gas supply unit 83 is attached to the second opening H9B of the operation portion 91. Gas flowing in from the second opening H9B is discharged to the renal pelvis 100 filled with the perfusate as bubbles from the first opening H9A of the distal end portion 90A through the internal space S91 of the operation portion 91 and the internal space S90 of the insertion portion 90. The gas discharged to the renal pelvis 100 is discharged to the outside of the body through the gap between the access sheath 70 and the insertion portion 90 together with the perfusate.

The T-shaped tube 84 is attached to a metal fitting of the insertion port H80B of the operation portion 91. A liquid supply tube of the liquid supply unit 85 is connected to the opening H84A of a side surface tube of the T-shaped tube 84. A supply amount of the perfusate is adjusted according to an opening and closing angle of a not-shown cock. As explained below, adjustment of the supply amount may be automatically performed by, for example, the processor 86.

The perfusate is injected into the renal pelvis 100 from the distal end opening H80A of the distal end portion 90A through the forceps channel 80. A treatment instrument 89 such as forceps or a laser probe is inserted into the forceps channel 80 from an opening H84B on the opposite side of the insertion port H80B of the T-shaped tube 84.

In order to prevent liquid from intruding into the internal space S90 of the insertion portion 90, the endoscope 9 preferably includes, between the first opening H9A and a flow passage, a gas-liquid separation film 50 that allows gas to permeate and does not allow liquid to permeate. The gas-liquid separation film 50 is, for example, a silicone porous film including very small holes, an outer diameter of which is smaller than approximately 0.5 micrometers.

The gas-liquid separation film 50 shown in FIG. 2 is disposed on a surface on a proximal end side of the distal end portion 90A. The gas-liquid separation film 50 may be disposed on a distal end face of the distal end portion 90A.

In the endoscope 9, the internal pressure of the renal pelvis 100 (pressure of the perfusate) is not directly measured using a sensor disposed in the renal pelvis 100. In other words, the sensor 60 that detects pressure is disposed in the operation portion 91 disposed on the outside of the body. The sensor 60 does not directly measure the pressure of the perfusate. The pressure of the perfusate in the renal pelvis 100 is estimated from measured pressure of fluid (gas) in the operation portion 91.

Figure 4:
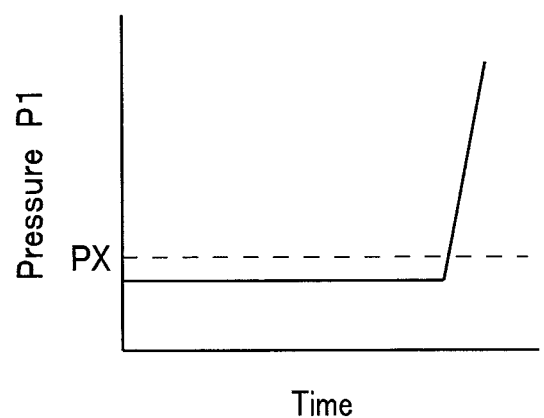
FIG. 4 is a diagram showing a pressure change detected by a pressure sensor in the endoscope system in the first embodiment.

As shown in FIG. 4, pressure of gas supplied from the gas supply unit 83 at a predetermined pressure and a predetermined flow rate F (pressure P1 detected by the sensor 60) sometimes suddenly rises. This is because an internal pressure P0 of the renal pelvis 100 becomes higher than pressure P2 of the gas discharged to the renal pelvis 100 and the gas is not discharged to the renal pelvis 100. In other words, the pressure P1 detected by the sensor 60 changes according to the pressure of the perfusate (the internal pressure P0) in the renal pelvis 100.

Pressure of fluid supplied from the gas supply unit 83 is set according to an allowed internal pressure P0. The pressure of the fluid is, for example, 40 cmH$_2$O.

A flow rate F of the fluid supplied from the gas supply unit 83 is set as appropriate. The flow rate F of the fluid is, for example, 5 cm$^3$/min.

For example, when the pressure P1 detected by the sensor 60 greatly rises or when the pressure P1 exceeds a predetermined value PX, the processor 86 controls the liquid supply unit 85 or the like to reduce a supply amount of the perfusate. For example, when the pressure P1 greatly rises, the processor 86 may emit a warning. In this case, a user adjusts, for example, an opening and closing angle of the cock of the T-shaped tube 84 based on the warning.

The pressure P2 is pressure of gas in the internal space S90 at the distal end portion 90A inserted into the renal pelvis 100. Since pressure of fluid flowing in the flow passage changes according to conduit resistance, the pressure P2 at the distal end portion 90A and the pressure P1 in the operation portion 91 are not the same. The conduit resistance is conspicuous when a sectional area of the flow passage is small.

In the endoscope 9, the flow passage of the gas is the internal space S91 of the operation portion 91 and the internal space S90 of the insertion portion 90. The internal space S91 and the internal space S9 have large sectional areas. Since the conduit resistance of the flow passage is small, the pressure P1 and the pressure P2 are substantially the same. Accordingly, the endoscope system 8 including the endoscope 9 can accurately estimate the internal pressure P0 of the renal pelvis 100.

In the endoscope 9, the sensor 60 is disposed not at the distal end portion 90A but in the operation portion 91. The endoscope 9 is minimally invasive because a distal end portion 91A has a small diameter.

Note that, although the conduit resistance increases, an exclusive tube may be disposed in the endoscope 9 as the flow passage of the gas for estimating the internal pressure of the renal pelvis 100. However, in the endoscope 9, since a wide space not used in a normal endoscope is used as the flow passage, it is unnecessary to dispose the exclusive tube. In other words, an inner surface of the flow passage of the gas is an inner wall 91S of the operation portion 91 and an inner wall 90S of the insertion portion 90. The endoscope 9 in which it is unnecessary to dispose the tube exclusive for the flow passage is minimally invasive because the insertion portion 90 has a small diameter.

Modification of the First Embodiment

Figure 5:
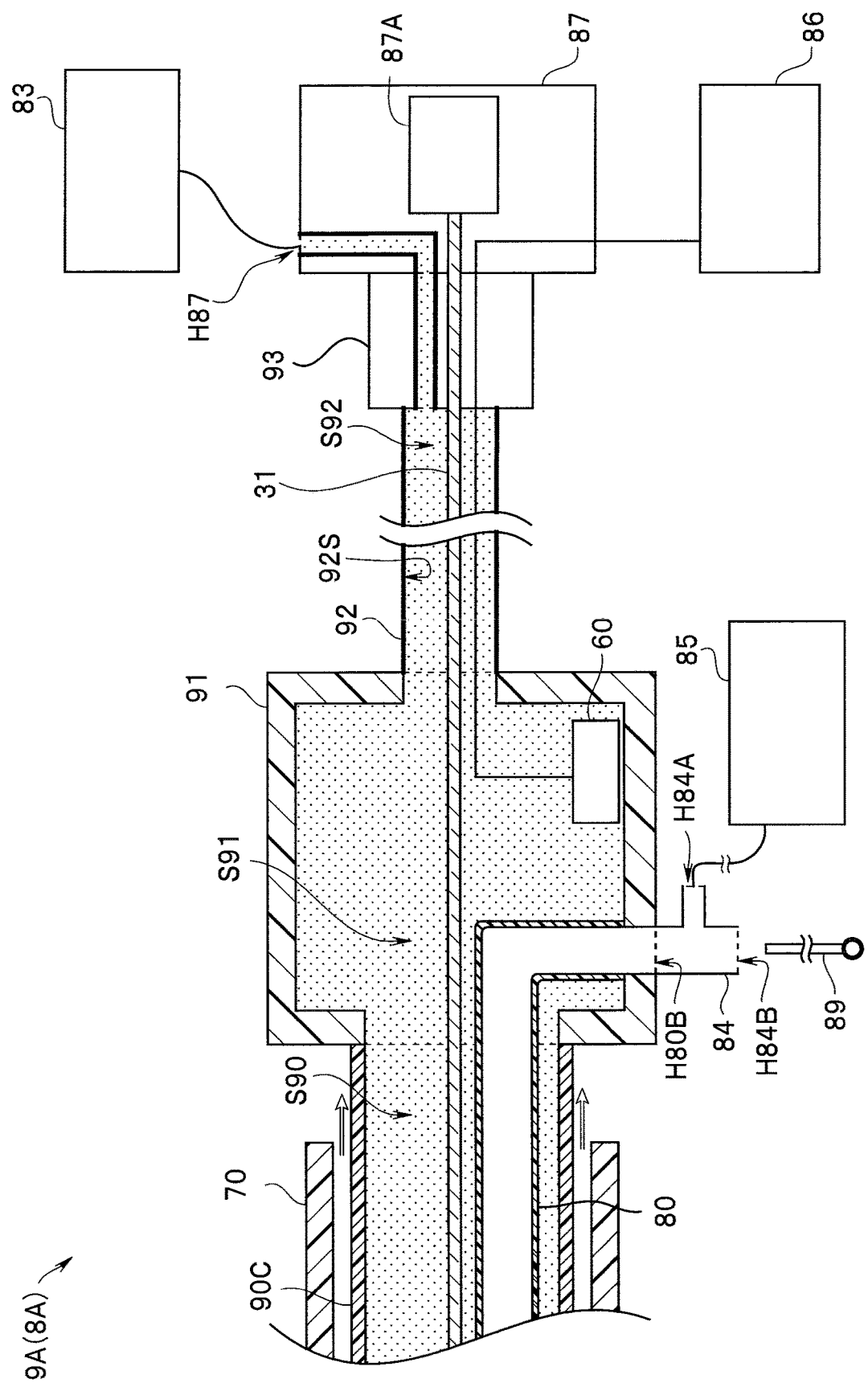
FIG. 5 is a sectional view of a main part of an endoscope system including an endoscope in a modification of the first embodiment.

As shown in FIG. 5, an endoscope 9A and an endoscope system 8A in a modification of the first embodiment are similar to the endoscope 9 and the endoscope system 8 in the first embodiment and have the same effects. Accordingly, in the following explanation, components having the same functions as the functions of the endoscope 9 and the endoscope system 8 are denoted by the same reference numerals and signs and explanation of the components is omitted. A configuration of a distal end portion of the endoscope 9A is the same as the configuration of the distal end portion of the endoscope 9. Therefore, the distal end portion is not shown in FIG. 5.

For example, an inner surface of an internal space S92 of the universal cord 92, which is a tube made of soft resin and mesh-like metal, is formed by an inner wall 92S of the tubular universal cord 92. The signal cable 22, the light guide 31, and the like are disposed in the internal space S92 of the universal cord 92. The internal space S92 of the universal cord 92 communicates with the internal space S91 of the housing of the operation portion 91 made of hard resin.

In the endoscope 9A, fluid is supplied to the light source apparatus 87 including a light source 87A from the gas supply unit 83. The fluid flowing into the internal space S92 of the universal cord 92 through the connector 93 is discharged to the renal pelvis 100 filled with the perfusate as bubbles from the first opening H9A of the distal end portion 90A through the internal space S91 of the operation portion 91 and the internal space S90 of the insertion portion 90.

The endoscope 9A and the endoscope system 8A have high operability because a gas feeding tube is not disposed in the operation portion 91. In the endoscope 9A and the endoscope system 8A, the fluid flows into the internal space S91 of the operation portion 91 using, as the flow passage, the internal space S92 of the universal cord 92 having a large sectional area. Therefore, a pressure loss in the universal cord 92 is small.

Second Embodiment

An endoscope 9B and an endoscope system 8B in a second embodiment are similar to the endoscope 9 and the endoscope system 8 in the first embodiment and have the same effects. Accordingly, components having the same functions as the functions of the endoscope 9 and the endoscope system 8 are denoted by the same reference numerals and signs and explanation of the components is omitted.

In the endoscope 9B, fluid for estimating internal pressure of the renal pelvis 100 is perfusate. As explained above, a flow passage of the perfusate is configured by a forceps channel 80B including the insertion port H80B in the operation portion 91 and including the distal end opening H80A at the distal end portion 90A.

Figure 6:
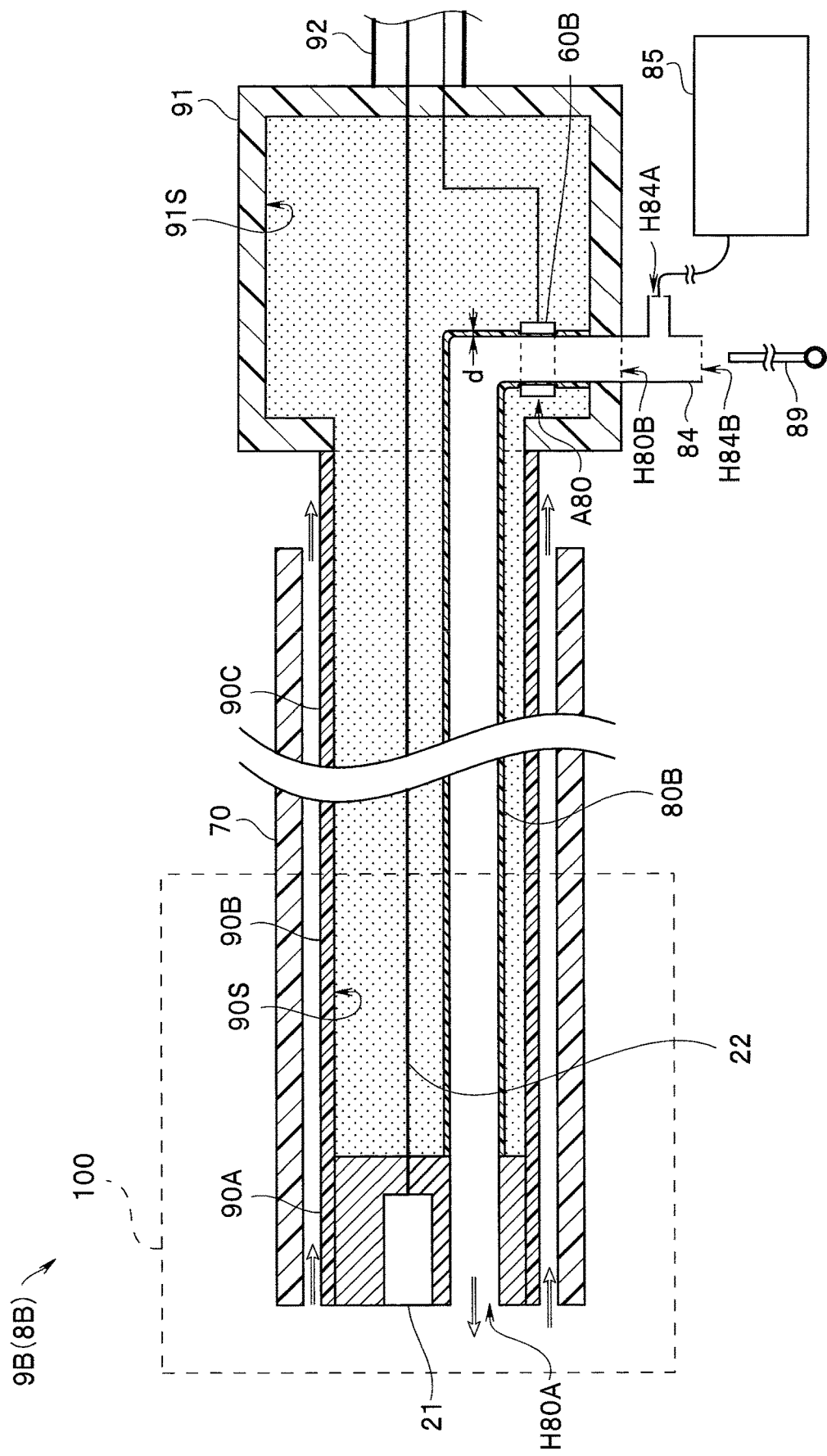
FIG. 6 is a sectional view of a main part of an endoscope system including an endoscope in a second embodiment.

As shown in FIG. 6, the forceps channel 80B made of an elastic body includes a thin detection region A80 in the operation portion 91. A sensor 60B is a strain gauge formed by, for example, a piezoelectric element and wound on an outer circumference of the detection region A80.

An outer diameter of the forceps channel 80B changes according to pressure of the perfusate. An outer diameter of the thin detection region A80 particularly greatly changes according to the pressure of the perfusate. Electric resistance of the sensor 60B changes when the outer diameter of the forceps channel 80B changes. Pressure detected by the sensor 60B is pressure of the perfusate in the forceps channel 80B in the operation portion 91. The pressure detected by the sensor 60B changes according to pressure of the perfusate in the renal pelvis 100 (a renal pelvis internal pressure). In the endoscope system 8B, a supply amount of the perfusate is controlled based on the pressure detected by the sensor 60B, whereby the renal pelvis internal pressure is properly adjusted.

Since the distal end portion 90A where a sensor is not disposed has a small diameter, the endoscope 9B and the endoscope system 8B are minimally invasive.

In the embodiments and the modification explained above, a flexible endoscope and a ureteropelvic endoscope system that estimate an internal pressure of a renal pelvis are explained as an example. The endoscopes in the embodiments of the present invention may be, for example, an endoscope for digestive organs or may be a rigid endoscope. Further, the endoscopes in the embodiments of the present invention may be an industrial endoscope or a wireless endoscope without a universal cord.

The present invention is not limited to the embodiment explained above. Various changes, alterations, and the like are possible within a range not changing the gist of the invention.

What is claimed is:
1. An endoscope comprising:
   an insertion portion comprising a distal end portion;

an operation portion connected to a proximal end of the insertion portion, the insertion portion and the operation portion having a channel having a first opening at the operation portion and a second opening at a distal end of the insertion portion, the operation portion and the insertion portion, excluding the channel, defining an internal space, the insertion portion further having a third opening at the distal end in communication with the internal space; and a sensor disposed in the operation portion and within the internal space, the sensor being configured to detect a pressure of gas passing through the internal space to the third opening, the third opening being configured to allow the gas in the internal space to flow out from the third opening.

2. The endoscope according to claim 1, wherein
the operation portion includes a fourth opening communicating with the internal space, and
the gas flows into the internal space through the fourth opening.

3. The endoscope according to claim 2, further comprising a gas-liquid separation film configured to allow the gas to permeate from the third opening and not allow liquid to permeate from the third opening.

4. The endoscope according to claim 3, further comprising a hole extending proximally from the third opening,
wherein the gas-liquid separation film is disposed proximally relative to the third opening.

5. The endoscope according to claim 1, wherein the internal space is a first internal space;
further comprising a universal cord disposed proximally relative to the operation portion, the universal cord having a second internal space in fluid communication with the first internal space;
wherein the gas flows into the first internal space from the second internal space of the universal cord.

6. The endoscope according to claim 5, further comprising a gas-liquid separation film configured to allow the gas to permeate from the third opening and not allow liquid to permeate from the third opening.

7. The endoscope according to claim 6, further comprising a hole extending proximally from the third opening,
wherein the gas-liquid separation film is disposed proximally relative to the third opening.

8. The endoscope according to claim 1, further comprising a sheath in which the insertion portion is inserted such that a gap is formed between an inner surface of the sheath and outer surface of the insertion portion;
wherein the gas flowing out from the third opening flows through the gap to an external space.

9. The endoscope according to claim 1, further comprising a gas-liquid separation film being configured to allow the gas to permeate from the third opening and not allow liquid to permeate from the third opening.

10. The endoscope according to claim 9, wherein
a hole extending proximally from the third opening,
the gas-liquid separation film is disposed at a proximal end of the hole.

11. The endoscope according to claim 1, further comprising:
an image pickup unit disposed in the distal end portion, and
the insertion portion being configured to be inserted into an organ of a subject.

12. An endoscope system comprising the endoscope according to claim 1, the endoscope system further comprising
a processor configured to control a supply amount of the gas based on the pressure detected by the sensor.

13. The endoscope system according to claim 12, wherein the processor is configured to reduce the supply amount when the pressure detected by the sensor exceeds a predetermined value.

14. An endoscope comprising:
an insertion portion comprising a distal end portion;
an operation portion connected at a proximal end of the insertion portion, the insertion portion and the operation portion having a channel having a first opening at the operation portion and a second opening at a distal end of the insertion portion; and
a sensor disposed in the operation portion, the sensor being configured to detect a pressure of a perfusate flowing through the channel, the sensor being positioned inside an internal space of the operation portion and outside of a flow path of the perfusate inside the channel.

15. The endoscope according to claim 14, further comprising
an image pickup unit disposed in the distal end portion; and
the insertion portion being configured to be inserted into an organ of a subject.

16. The endoscope according to claim 14, wherein the insertion portion being configured to be inserted into an organ of a subject;
further comprising a sheath in which the insertion portion is inserted;
wherein the perfusate flowing out from the second opening overflows from the organ and through a gap between an inner surface of the sheath and outer surface of the insertion portion to an external space.

17. The endoscope according to claim 14, wherein
the channel includes a detection region, and
the sensor is a strain gauge disposed on an outer circumference of the detection region.

18. The endoscope according to claim 17, wherein an outer diameter of the detection region is smaller than an outer diameter of other portion of the channel.

19. The endoscope according to claim 17, wherein the sensor is wound on the outer circumference of the detection region.

20. An endoscope system comprising the endoscope according to claim 14, the endoscope system further comprising a processor configured to control a supply amount of the perfusate based on the pressure detected by the sensor.

* * * * *